(12) United States Patent
Perez et al.

(10) Patent No.: US 8,047,207 B2
(45) Date of Patent: Nov. 1, 2011

(54) ORIFICE INSERTION DEVICES AND METHODS

(75) Inventors: Moises Perez, Miami, FL (US); John Patrick Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 162 days.

(21) Appl. No.: 12/196,884

(22) Filed: Aug. 22, 2008

(65) Prior Publication Data

US 2009/0071486 A1    Mar. 19, 2009

Related U.S. Application Data

(60) Provisional application No. 60/957,177, filed on Aug. 22, 2007.

(51) Int. Cl.
*A61F 11/00* (2006.01)
*H04R 25/00* (2006.01)
*H04R 25/02* (2006.01)
*A61B 7/02* (2006.01)

(52) U.S. Cl. ........ 128/864; 128/868; 181/129; 181/130; 181/135; 381/328

(58) Field of Classification Search .................. 128/864, 128/865, 866, 867, 868; 181/129, 130, 135, 181/467, 464, 466, 128; 381/71.1, 312, 328
See application file for complete search history.

(56) References Cited

U.S. PATENT DOCUMENTS

| | | | |
|---|---|---|---|
| 2,535,258 A | 12/1950 | Bland | |
| 3,602,654 A | 8/1971 | Victoreen | |
| 4,133,984 A * | 1/1979 | Akiyama | 381/328 |
| 4,741,344 A | 5/1988 | Danby et al. | |
| 4,834,211 A | 5/1989 | Bibby et al. | |
| 4,896,679 A | 1/1990 | St. Pierre | |
| 4,962,537 A | 10/1990 | Basel et al. | |
| 5,333,622 A | 8/1994 | Casali et al. | |
| 5,483,027 A * | 1/1996 | Krause | 181/135 |
| 6,094,494 A | 7/2000 | Haroldson | |
| 6,256,396 B1 | 7/2001 | Cushman | |
| 6,339,648 B1 * | 1/2002 | McIntosh et al. | 381/328 |
| 6,393,130 B1 | 5/2002 | Stonikas et al. | |
| 6,671,381 B1 | 12/2003 | Lux-Wellenhof | |
| 7,130,437 B2 | 10/2006 | Stonikas et al. | |
| 7,164,775 B2 | 1/2007 | Meyer et al. | |
| 7,227,968 B2 | 6/2007 | van Halteren et al. | |
| 7,362,875 B2 | 4/2008 | Saxton et al. | |
| 7,387,187 B2 | 6/2008 | Widmer et al. | |
| 2006/0159298 A1 | 7/2006 | von Dombrowski et al. | |
| 2007/0116319 A1 | 5/2007 | Hagberg | |
| 2008/0144871 A1 | 6/2008 | Purcell et al. | |
| 2009/0173353 A1 | 7/2009 | Purcell et al. | |
| 2009/0221933 A1* | 9/2009 | Nishtala et al. | 600/561 |
| 2009/0320858 A1 | 12/2009 | Purcell et al. | |
| 2009/0320859 A1 | 12/2009 | Purcell et al. | |

* cited by examiner

*Primary Examiner* — Patricia Bianco
*Assistant Examiner* — Ophelia Hawthorne
(74) *Attorney, Agent, or Firm* — RatnerPrestia

(57) ABSTRACT

Methods and devices for sealing an orifice are provided. A sealing element is inserted into an orifice. A fluid is transferred into the sealing element. Fluid transfer into the sealing element is restricted when a pressure in the sealing element is greater than a threshold value.

18 Claims, 5 Drawing Sheets

700

740

ORIFICE INSERTION DEVICES AND METHODS

CROSS-REFERENCE TO RELATED APPLICATIONS

This application claims the benefit of U.S. provisional patent application No. 60/957,177 filed on 22 Aug. 2007. The disclosure of which is incorporated herein by reference in its entirety.

FIELD OF THE INVENTION

The present invention relates to orifice sealing, and more particularly, though not exclusively, to inflatable and other sealing configurations of earpieces.

BACKGROUND OF THE INVENTION

Contemporary earpieces and orifice sealing devices utilize foam and/or flexible low durometer material, which can provide sound isolation if fitted properly. However fitting properly is a problem with current systems. A system that can expand or contract to fit most orifices (e.g., ear canals, nose, veins, pipes) would be useful.

SUMMARY OF THE INVENTION

In one embodiment, the invention provides a method of sealing an orifice wherein a sealing element is inserted into the orifice. A fluid is transferred into the sealing element. Fluid transfer into the sealing element is restricted when a pressure in the sealing element is greater than a threshold value.

In another embodiment, the invention provides an orifice sealing device having a sealing element configured to be inserted into the orifice. A fluid transfer element is configured to pass fluid to and from the sealing element until the sealing element reaches a pressure. The device further includes a fluid reservoir to and from which fluid can be passed to control the pressure.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS OF THE PRESENT INVENTION

Figure 1:
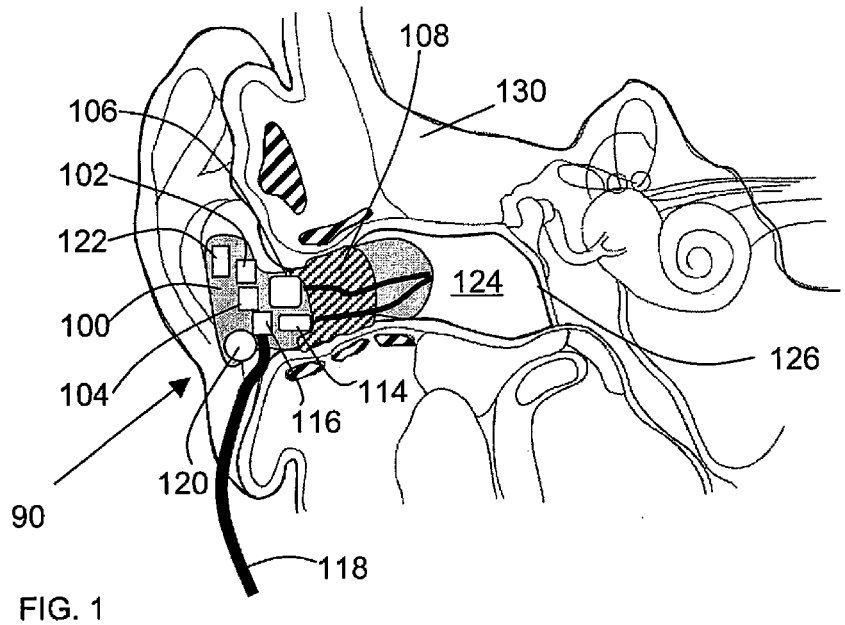
FIG. 1 illustrates an earpiece in accordance with at least one exemplary embodiment.

The following description of exemplary embodiment(s) is merely illustrative in nature and is in no way intended to limit the invention, its application, or uses.

Exemplary embodiments are directed to or can be operatively used on various orifice insertion devices, wired or wireless (e.g., earbuds, headphones, ear terminals, behind the ear devices, nasal inserts, anal, vein and artery inserts or other such devices as known by one of ordinary skill, and equivalents).

Processes, techniques, apparatus, and materials as known by one of ordinary skill in the art may not be discussed in detail but are intended to be part of the enabling description where appropriate. For example specific computer code may not be listed for achieving each of the steps discussed, however one of ordinary skill would be able, without undo experimentation, to write such code given the enabling disclosure herein. Such code is intended to fall within the scope of at least one exemplary embodiment.

Additionally exemplary embodiments are not limited to earpieces, for example some functionality can be implemented on other systems with speakers and/or microphones for example computer systems, PDAs, BlackBerry® Smartphones, cell and mobile phones, and any other device that emits or measures acoustic energy. Additionally, exemplary embodiments can be used with digital and non-digital acoustic systems. Additionally various receivers and microphones can be used, for example MEMs transducers, diaphragm transducers, for example Knowles' FG and EG series transducers.

Notice that similar reference numerals and letters refer to similar items in the following figures, and thus once an item is defined in one figure, it may not be discussed or further defined in the following figures.

At least one exemplary embodiment is directed to a method of sealing an earpiece comprising: pumping a fluid (e.g., air, gas, fluid, gel) into an inflatable membrane (e.g., balloon, a membrane attached to one end and expandable on another), where the inflatable membrane is operatively attached (e.g., a non-expandable part glued to a support structure, while the expandable portion expands toward the ear canal wall) to an earpiece (e.g., earbuds, ear terminals, behind the ear devices, hearing aids, and any other device that directs acoustic energy into the ear canal); measuring the pressure change (e.g., via a pressure transducer hooked up to a bleed channel, where the pressure in a bladder directly or entering the bladder is measured by the pressure transducer) in the membrane; and activating (e.g., sending a voltage to the control circuit of a mini valve to open or close) a valve when the rate of pressure change (e.g., the pressure measured by the transducer is saved versus time, at a sampling rate (e.g., 20 Hz) and the serial pressure values are differenced to obtain a rate of pressure change) reaches a threshold value (e.g., when the rate of change is 3 mg/cm^2/sec, where the pressure can be converted into Pascals by converting cm to meters and replacing mg with kg times gravitational acceleration), where the valve activation closes off (e.g., the valve physically closes off the feed channel, for example a physical barrier or pinches a flexible tubing) the fluid flow. Additionally a flexible restoring element (e.g., elastic bladder, mechanical actuator) can be used that expands when the device is inserted into an orifice with an opening smaller than the inflatable membrane, the fluid in the membrane will flow back into a reservoir encompassed at least in part by the restoring element. Thus when a certain pressure is obtained upon insertion or removal from the orifice, the fluid expands the reservoir. When the smaller area is passed and the inflatable membrane can expand again, the restoring element's exerted force will force the fluid to flow back into the inflatable membrane.

Note that the pressure contained by the membrane can be reduced after the rate of pressure change reaches a second rate of pressure change (e.g., 1 mg/cm^2/sec). For example when during expansion a detector detects resistance from the ear canal wall (rate of pressure increase changes) the pressure may be too large for comfort, thus a little fluid is allowed to bleed a certain amount (e.g., into a reservoir).

At least one further exemplary embodiment varies the pumping pressure after measuring the NRR. For example measuring the difference in the acoustic signal received by the ASM and the ECM, and if the NRR is below a third threshold level (e.g., 15 dB) increasing the pressure in the inflatable membrane until greater than the thresholds are achieved.

At least one exemplary embodiment includes a method of sealing an orifice comprising: inserting (e.g., deflating the inflatable membrane to a diameter smaller than the orifice inner diameter) a sealing element (e.g., the inflatable membrane attached to a tube feeding a fluid (gas or fluid) into an orifice (e.g., ear canal, pipe, nasal, anal); transferring a fluid (e.g., air, water, alcohol, gel particles suspended in liquid, gas, liquid) into the sealing element; and restricting fluid transfer (e.g., via a mechanical valve, via backpressure exerted by the inflatable membrane) into the sealing element when a pressure (e.g., absolute pressure, gauge pressure) in the sealing element is greater than a threshold value (e.g., 1 bar). For example if during insertion the inflatable membrane size (e.g., diameter, cross sectional area) is larger than the orifice inner diameter (note that the orifice can have an irregular cross section as well) then when inserted the pressure of the inner portion of the wall of the orifice can push fluid back out of the inflatable membrane (e.g., via a channel inside a support tube, or outside the support tube). Note that in at least one exemplary embodiment the threshold value can be a value between 0.04 bar and 2.4 bar.

In at least one exemplary embodiment the step of restricting the fluid can be a reservoir where the fluid moves out of the sealing element when the pressure is greater than the threshold value. For example if during insertion and extraction a pressure is exerted against the inflatable membrane then when a certain value is reached (or immediately upon application of a force) the fluid can move from the inflatable membrane into a restoring system that can be a restoring elastic membrane, or a bladder with a restoring mechanical element (e.g., spring pressing against bladder with a designed equivalent pressure (e.g., ½ threshold value).

Note in at least one exemplary embodiment the sealing element can be a non-expandable balloon (e.g., one that originally has a shape that expands little (e.g., 10%) from this shape but can be compressed) that has an initial size and shape and can be compressed but not substantially expanded beyond the initial size and shape. Additionally the sealing element (e.g., inflatable membrane) can be an expandable balloon or expandable polymer.

In at least one exemplary embodiment the step of transferring a fluid moves fluid through an interior channel of a tube feeding the sealing element. For example the inflatable membrane can form an expandable balloon through which or into which a tube feeds fluid. The fluid can be fed through the inside of the tube (e.g., via ports inside the balloon, or from outside the tube (e.g., small outer channel on the tube outside fitting under the balloon (where the channel and the balloon have been sealed to the tube).

At least one exemplary embodiment of the invention is directed to an earpiece that directs acoustic energy into the ear canal and samples acoustic energy from the ear canal. Reference is made to FIG. 1 in which an earpiece device, generally indicated as earpiece 90, is constructed and operates in accordance with at least one exemplary embodiment of the invention. As illustrated, earpiece 90 comprises an electronic housing unit 100 and a sealing unit 108. Earpiece 90 depicts an electro-acoustical assembly for an in-the-ear acoustic assembly, as it would typically be placed in an ear canal 124 of a user 130. The earpiece 90 can be an in the ear earpiece, behind the ear earpiece, receiver in the ear, partial-fit device, or any other suitable earpiece type. The earpiece 90 can be partially or fully occluded in ear canal 124, and is suitable for use with users having healthy or abnormal auditory functioning.

In one exemplary embodiment, earpiece 90 includes an Ambient Sound Microphone (ASM) 120 to capture (measure) ambient sound (acoustic energy), an Ear Canal Receiver (ECR) 114 to deliver audio (acoustic energy) to an ear canal 124, and an Ear Canal Microphone (ECM) 106 to capture and assess a sound exposure level within the ear canal 124. The earpiece 90 can partially or fully occlude the ear canal 124 to provide various degrees of acoustic isolation. The assembly is designed to be inserted into the user's ear canal 124, and to form an acoustic seal with the walls of the ear canal 124 at a location between the entrance to the ear canal 124 and the tympanic membrane 126 (or eardrum). In general, such a seal is typically achieved by means of a soft and compliant housing of sealing unit 108.

Sealing unit 108 can be an acoustic barrier (e.g., producing acoustic isolation or reducing acoustic energy across the sealing unit), having a first side coupled to ear canal 124 and a second side coupled to the ambient region or ambient environment. In at least one exemplary embodiment, sealing unit 108 includes at least one acoustic tube. The at least one acoustic tube is an acoustic pathway for receiving or delivering audio content. Sealing unit 108 can create a closed cavity of (e.g., approximately 5 cc) between the first side of sealing unit 108 and the tympanic membrane 126 in ear canal 124. As a result of this sealing, the ECR (speaker) 114 is able to generate a full range bass response when reproducing sounds for the user. This seal also serves to significantly reduce the sound pressure level at the user's eardrum 126 resulting from the sound field at the entrance to the ear canal 124. This seal is also a basis for a passive sound isolating performance of the electro-acoustic assembly.

In at least one exemplary embodiment and in broader context, the second side of sealing unit 108 corresponds to earpiece 90, and is operatively connected to electronic housing unit 100, and ambient sound microphone 120 that is exposed to the ambient environment. Ambient sound microphone 120 receives ambient sound from the ambient region around the user.

Electronic housing unit 100 houses system components such as a microprocessor 116, memory 104, battery 102, ECM 106, ASM 120, ECR 114, and user interface 122. Microprocessor 116 can be a logic circuit, a digital signal processor, controller, or the like for performing calculations and operations for earpiece 90. Microprocessor 116 is operatively coupled to memory 104, ECM 106, ASM 120, ECR 114, and user interface 122. A wire 118 provides an external connection to earpiece 90. Battery 102 powers the circuits and transducers of earpiece 90. Battery 102 can be a rechargeable or replaceable battery.

One function of ECM 106 is that of measuring the sound pressure level in the ear canal cavity 124 as a part of testing the hearing acuity of the user as well as confirming the integrity of the acoustic seal and the working condition of the earpiece 90. In one arrangement, ASM 120 is housed in an ear seal of earpiece 90 to monitor sound pressure at the entrance to the occluded or partially occluded ear canal 124. All transducers shown can receive or transmit audio electrical signals to microprocessor 116 (hereinafter processor 116) that undertakes audio signal processing and provides a transceiver for audio via the wired (wire 118) or a wireless communication path.

In at least one exemplary embodiment, earpiece 90 can actively monitor a sound pressure level both inside and outside an ear canal 124 and enhance spatial and timbral sound quality while maintaining supervision to ensure safe sound reproduction levels. The earpiece 90 in various embodiments can conduct listening tests, filter sounds in the environment, monitor warning sounds in the environment, present notification based on identified warning sounds, maintain constant audio content to ambient sound levels, and filter sound in accordance with a Personalized Hearing Level (PHL).

The earpiece 90 can generate an Ear Canal Transfer Function (ECTF) to model the ear canal 124 using ECR 114 and ECM 106, as well as an Outer Ear Canal Transfer function (OETF) using ASM 120. For instance, the ECR 114 can deliver an impulse within the ear canal 124 and generate the ECTF via cross correlation of the impulse with the impulse response of the ear canal 124. The earpiece 90 can also determine a sealing profile with the user's ear to compensate for any leakage. It also includes a Sound Pressure Level Dosimeter to estimate sound exposure and recovery times. This permits the earpiece 90 to safely administer and monitor sound exposure to the ear.

Figure 2:
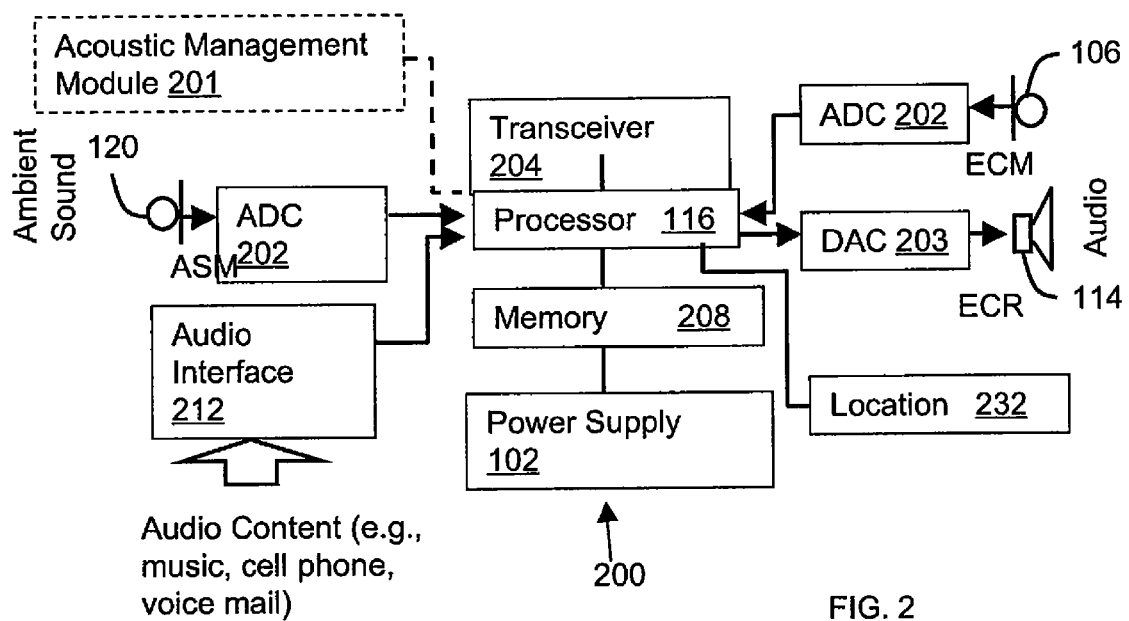
FIG. 2 is a block diagram of circuitry and components of an earpiece in accordance with at least one exemplary embodiment.

Referring to FIG. 2, a block diagram 200 of the earpiece 90 in accordance with an exemplary embodiment is shown. As illustrated, the earpiece 90 can include the processor 116 operatively coupled to the ASM 120, ECR 114, and ECM 106 via one or more Analog to Digital Converters (ADC) 202 and Digital to Analog Converters (DAC) 203. The processor 116 is configured operatively with storage memory 208 whereby storage memory 208 can be a Flash, ROM, RAM, SRAM, DRAM or other storage methods as know by one of ordinary skill. The processor 116 can also include a clock to record a time stamp.

As illustrated, the earpiece 90 can include an acoustic management module 201 to mix sounds captured at the ASM 120 and ECM 106 to produce a mixed sound. The processor 116 can then provide the mixed signal to one or more subsystems, such as a voice recognition system, a voice dictation system, a voice recorder, or any other voice related processor or communication device. The acoustic management module 201 can be a hardware component implemented by discrete or analog electronic components or a software component. In one arrangement, the functionality of the acoustic management module 201 can be provided by way of software, such as program code, assembly language, or machine language.

The memory 208 can also store program instructions for execution on the processor 116 as well as captured audio processing data and filter coefficient data. The memory 208 can be off-chip and external to the processor 208, and include a data buffer to temporarily capture the ambient sound and the internal sound, and a storage memory to save from the data buffer the recent portion of the history in a compressed format responsive to a directive by the processor. The data buffer can be a circular buffer that temporarily stores audio sound at a current time point to a previous time point. It should also be noted that the data buffer can in one configuration reside on the processor 116 to provide high speed data access. The storage memory can be non-volatile memory such as SRAM to store captured or compressed audio data.

The earpiece 90 can include an audio interface 212 operatively coupled to the processor 116 and acoustic management module 201 to receive audio content, for example from a media player, cell phone, or any other communication device, and deliver the audio content to the processor 116. The processor 116 is responsive to detecting spoken voice from the acoustic management module 201 and can adjust the audio content delivered to the ear canal. For instance, the processor 116 (or acoustic management module 201) can lower a volume of the audio content responsive to detecting a spoken voice. The processor 116 by way of the ECM 106 can also actively monitor the sound exposure level inside the ear canal and adjust the audio to within a safe and subjectively optimized listening level range based on voice operating decisions made by the acoustic management module 201.

The earpiece 100 can further include a transceiver 204 that can support singly or in combination any number of wireless access technologies including without limitation Bluetooth™, Wireless Fidelity (WiFi), Worldwide Interoperability for Microwave Access (WiMAX), and/or other short or long range communication protocols. The transceiver 204 can also provide support for dynamic downloading over-the-air to the earpiece 90. It should be noted also that next generation access technologies can also be applied to the present disclosure.

The location receiver 232 can utilize common technology such as a common GPS (Global Positioning System) receiver that can intercept satellite signals and therefrom determine a location fix of the earpiece 90.

In at least one exemplary embodiment, the power source (e.g., battery) 102 can be a rechargeable or replaceable battery but more generally it can be a power source utilizing common power management technologies such as supply regulation technologies, and charging system technologies for supplying energy to the components of the earpiece 90 and to facilitate portable applications. A motor (not shown) can be a single supply motor driver coupled to the power supply 102 to improve sensory input via haptic vibration. As an example, the processor 116 can direct the motor to vibrate responsive to an action, such as a detection of a warning sound or an incoming voice call.

The earpiece 90 can further represent a single operational device or a family of devices configured in a master-slave arrangement, for example, a mobile device and an earpiece. In the latter embodiment, the components of the earpiece 90 can be reused in different form factors for the master and slave devices.

Figure 3:
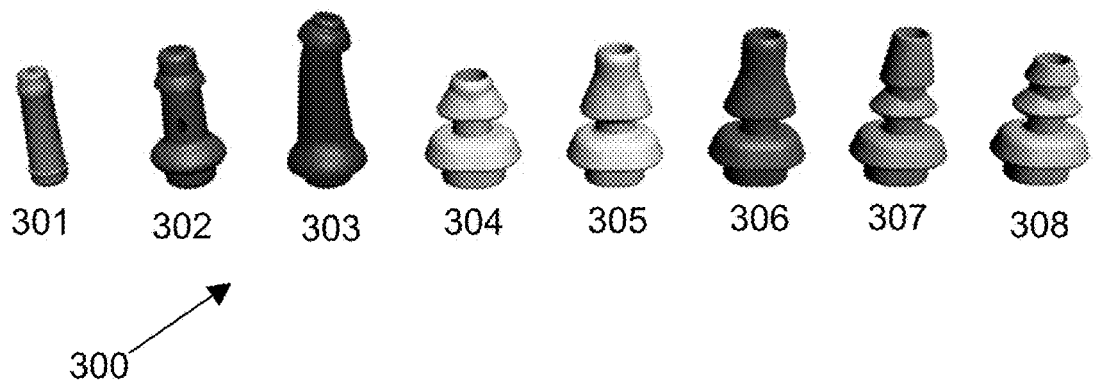
FIG. 3 illustrates various tubes that can support a sealing section or whom themselves are sealing sections in accordance with at least one exemplary embodiment.

FIG. 3 illustrates various tubes 300 (e.g., 301, 302, 303, 304, 305, 306, 307, 308) that can support a sealing section or whom themselves are sealing sections in accordance with at least one exemplary embodiment. For example 301 is cylindrical with a sloped contour for grip and facilitates "snaking" through metal bends. 302 has a conical shape with a gel filled base and a soft end flange for sealing. 303 has a round-oval cross section with a tapered end flange for sealing. 304 has a square-oval cross section with a soft base flange for aperture sealing and a semi-solid plug for deeper metal sealing. 305 has a steeper plug angle and a longer nose for deeper insertion. 306 is a longer version of 305 with ports allocated for an inflatable portion. 307 has a tri-level flange design intended to add additional security and retention while improving sealing. 308 is a smaller version of design 307 with a sharper plug for greater sealing.

Figure 4:
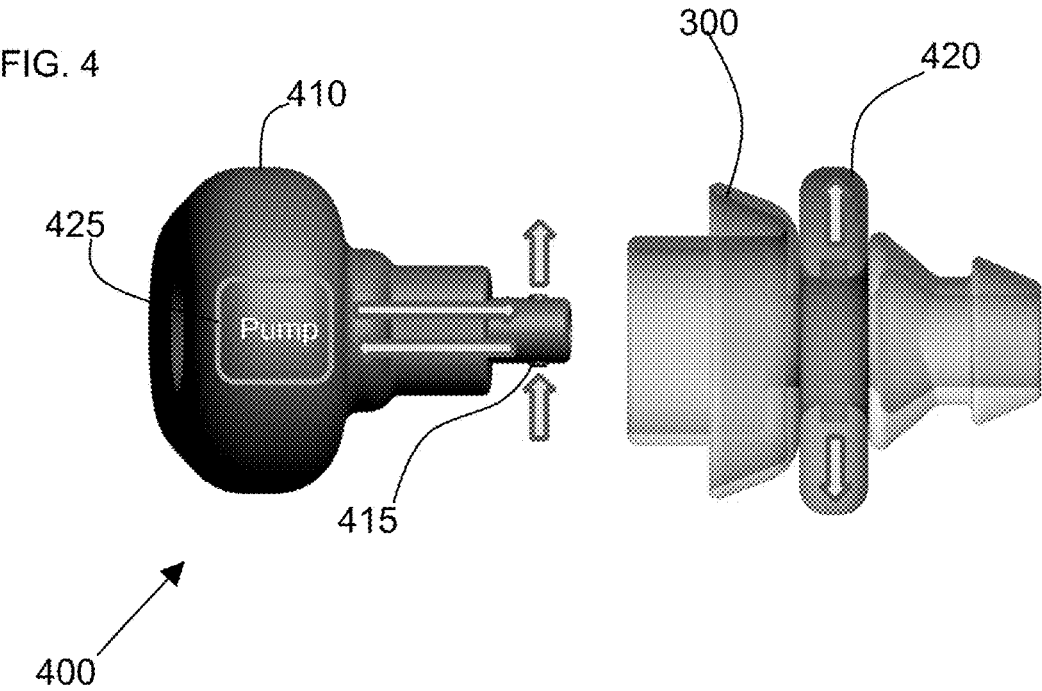
FIG. 4 illustrates at least one configuration of an orifice insertion device according to at least one exemplary embodiment.

FIG. 4 illustrates at least one configuration 400 of an orifice insertion device according to at least one exemplary embodiment. Chassis 410 having pump 425 can be sealed with routed tubing leading to exit ports 415 through which fluid (e.g., gas, liquid) can flow out of or into the inflatable membrane 420, which can be supported by a tube 300. Exit ports 415 can have a "squeeze fit" with the silicon tip (e.g., tube 300) allowing the fluid (e.g., air) pressure to flow into the over-molded inflatable member 420. Note with no "extreme" bending (e.g., 360 degree bend) the seal will maintain itself. Optionally o-rings or gaskets can be added.

Figure 5A:
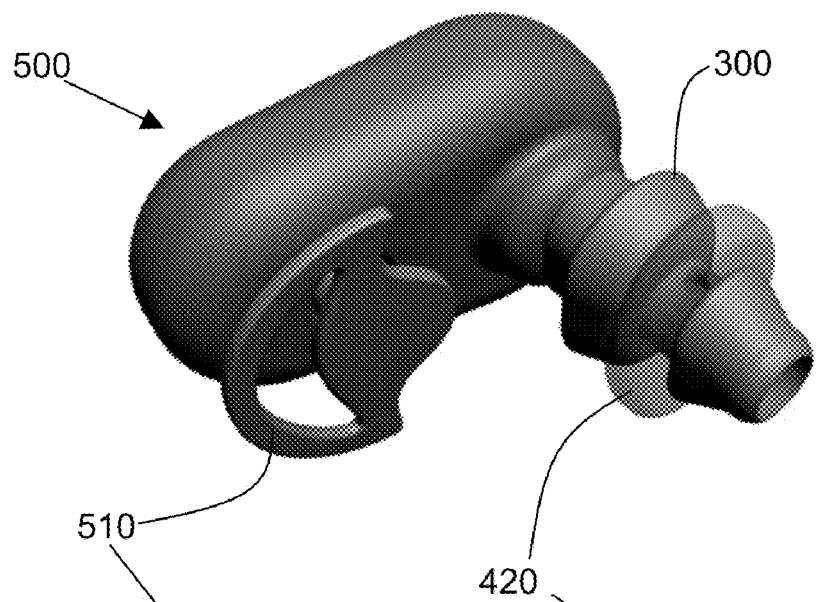
FIGS. 5A and 5B illustrate at least one configuration of an orifice insertion device according to at least one exemplary embodiment.
Figure 5B:
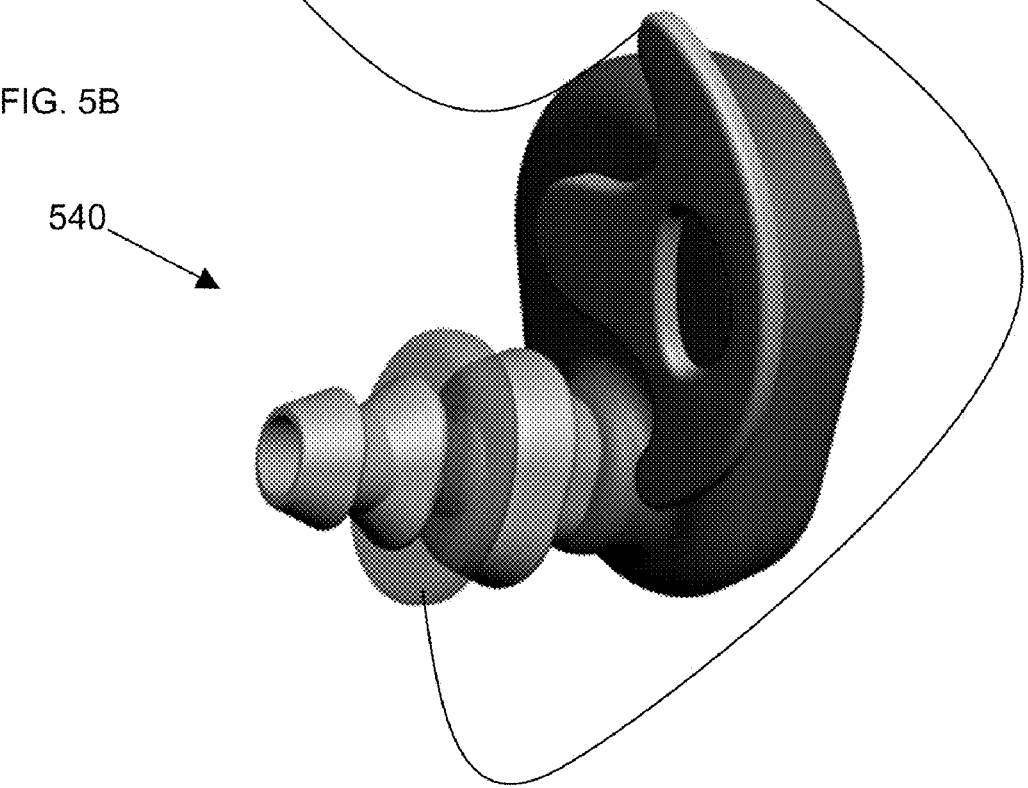

FIGS. 5A and 5B illustrates at least one configuration (e.g., 500 and 540) of an orifice insertion device according to at least one exemplary embodiment. This configuration is configured to fit into the concha of an ear for example a concha securing device 510 can be used to secure and add stability.

Figure 6A:
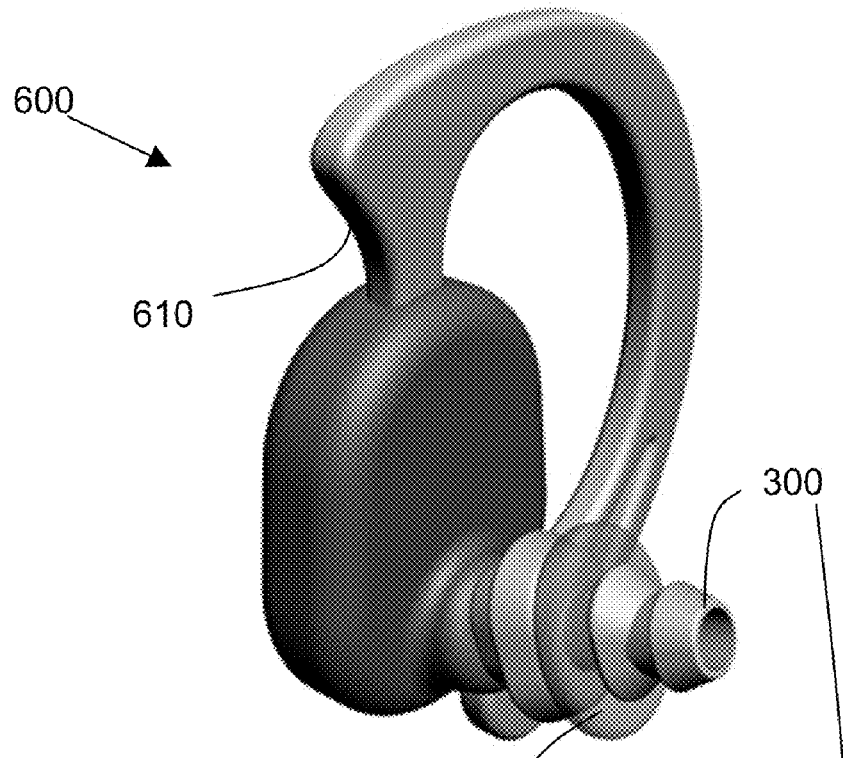
FIGS. 6A and 6B illustrate at least one configuration of an orifice insertion device according to at least one exemplary embodiment.
Figure 6B:
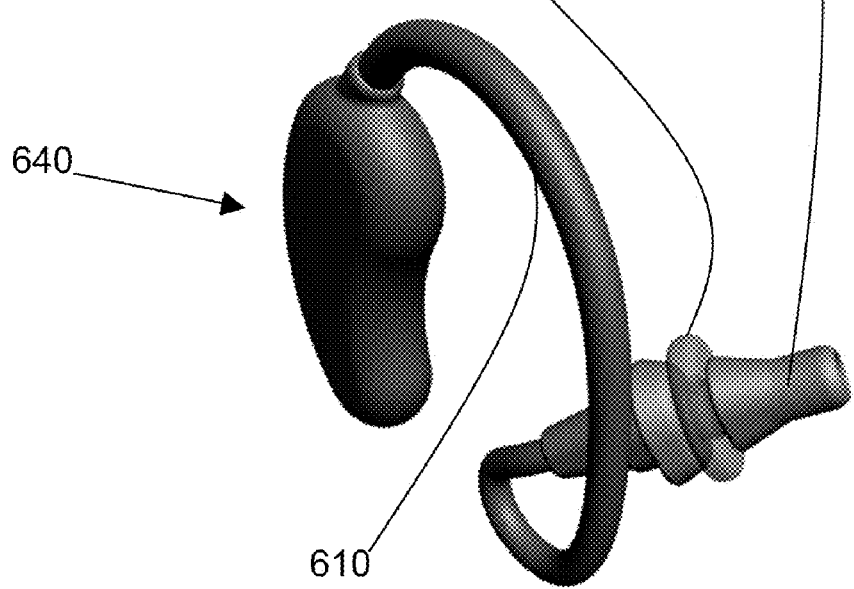

FIGS. 6A and 6B illustrates at least one configuration (600 and 640) of an orifice insertion device according to at least one exemplary embodiment. This configuration is configured to fit with a support behind the ear for example a behind the ear securing device 610 can be used to secure and add stability.

Figure 7A:
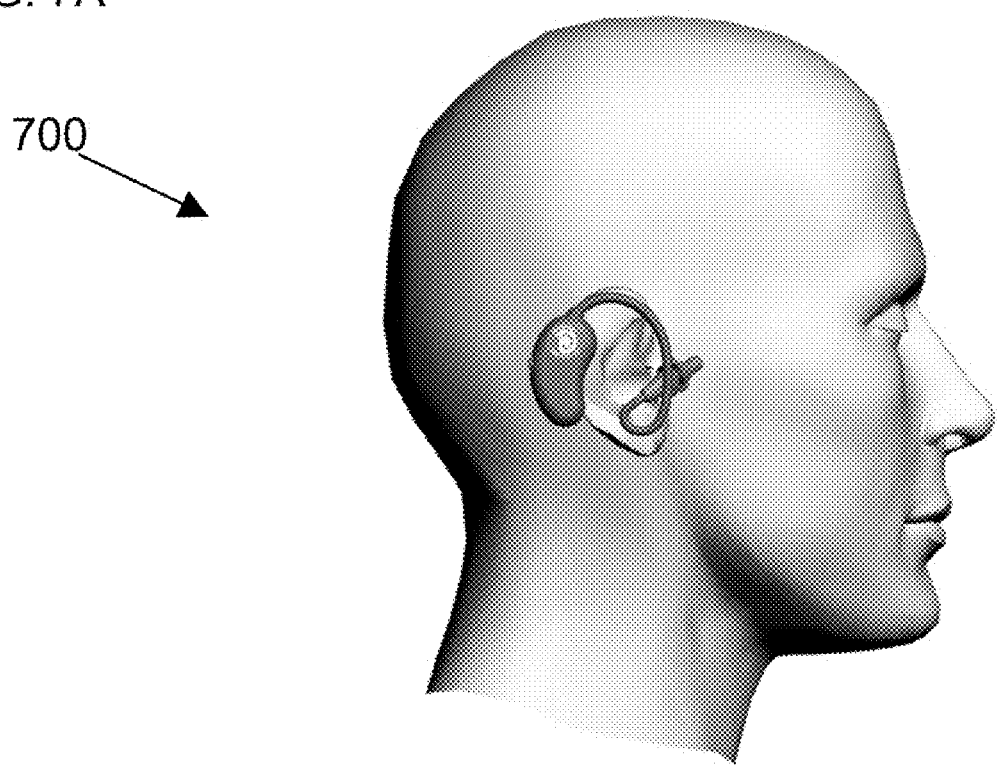
FIGS. 7A and 7B illustrate various configurations according to at least one exemplary embodiment.

FIG. 7A illustrates a user wearing a behind the ear device 700 in accordance with at least one exemplary embodiment. Note one earpiece or two can be worn.

Figure 7B:
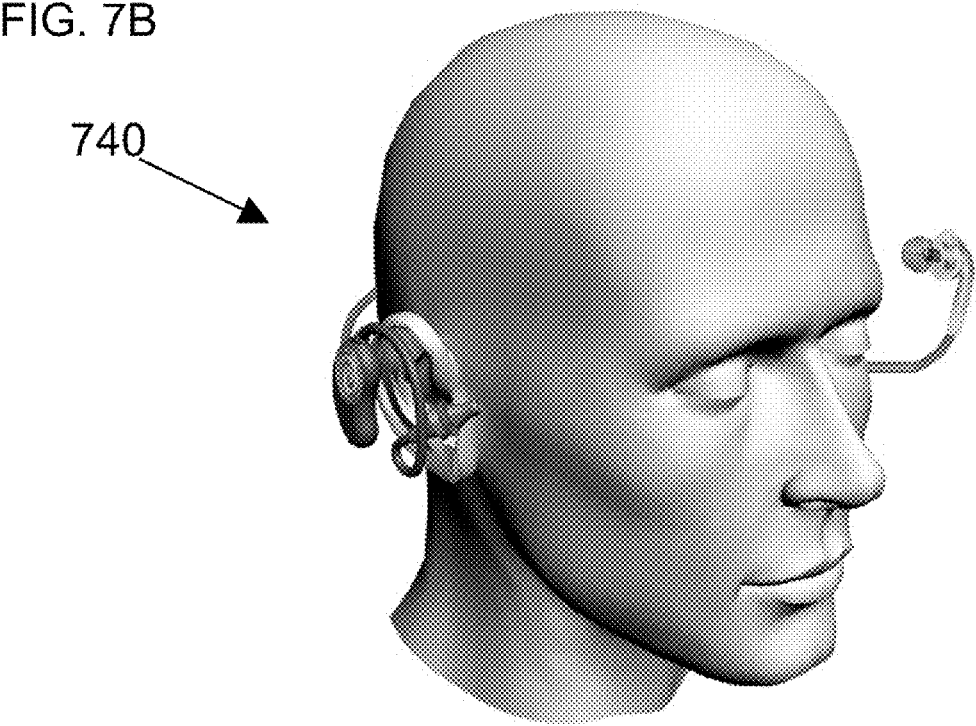

FIG. 7B illustrates a configuration 740 where a main earpiece is worn and a slave earpiece is attached.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments.

Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. A method of sealing an ear canal comprising:
   inserting a sealing element into an ear canal;
   transferring a fluid into the sealing element to seal the ear canal;
   measuring a change of pressure in the sealing element responsive to the transferring of the fluid into the sealing element; and
   activating a valve to prevent fluid transfer into the sealing element when the measured change of pressure is greater than a threshold value.

2. The method according to claim 1, wherein the measuring of the change of pressure includes measuring a gauge pressure.

3. The method according to claim 2, wherein the threshold value is between 0.04 bar and 2.4 bar.

4. The method according to claim 1, wherein the sealing element includes a non-expandable balloon having an initial size and shape, the non-expandable balloon configured to be compressed but not substantially expanded beyond the initial size and shape.

5. The method according to claim 1, wherein the sealing element includes an expandable balloon.

6. The method according to claim 1, wherein the sealing element includes an expandable polymer.

7. The method according to claim 1, wherein the transferring of the fluid includes moving the fluid through an interior channel of a tube feeding the sealing element.

8. The method according to claim 1, wherein the transferring of the fluid includes moving the fluid from outside a tube feeding the sealing element.

9. The method according to claim 1, wherein the fluid is at least one of a gas, a liquid, and a mixture of liquid and suspended particles.

10. An ear canal sealing device comprising:
    a sealing element configured to be inserted into an ear canal;
    a fluid transfer element configured to pass transfer fluid into the sealing element to seal the ear canal;
    a pressure measurement device configured to measure a change of pressure in the sealing element responsive to the transferring of the fluid into the sealing element; and
    a valve configured to be activated to prevent fluid transfer into the sealing element when the measured change of pressure is greater than a threshold value.

11. The device according to claim 10, wherein the pressure is measurement device is configured to measure a gauge pressure.

12. The device according to claim 10, wherein the threshold value is between 0.04 bar and 2.4 bar gauge.

13. The device according to claim 10, wherein the sealing element includes a non-expandable balloon having an initial size and shape, the non-expandable balloon configured to be compressed but not substantially expanded beyond the initial size and shape.

14. The device according to claim 10, wherein the sealing element includes an expandable balloon.

15. The device according to claim 10, wherein the sealing element includes an expandable polymer.

16. The device according to claim 10, wherein the fluid transfer element is an interior channel of a tube feeding the sealing element.

17. The device according to claim 10, wherein the fluid transfer element is a channel outside a tube feeding the sealing element.

18. The device according to claim 10, wherein the fluid is at least one of a gas, a liquid, and a mixture of liquid and suspended particles.

* * * * *